(12) United States Patent
Maor et al.

(10) Patent No.: US 6,612,988 B2
(45) Date of Patent: Sep. 2, 2003

(54) ULTRASOUND THERAPY

(75) Inventors: Dov Maor, Haifa (IL); Javier Grinfeld, Haifa (IL); Kullervo Hynynen, Medfield, MA (US)

(73) Assignees: Brigham and Women's Hospital, Inc., Boston, MA (US); InSightec - Image Guided Treatment Ltd., Tirat Carmel (IL)

(*) Notice: Subject to any disclaimer, the term of this patent is extended or adjusted under 35 U.S.C. 154(b) by 55 days.

(21) Appl. No.: 09/738,514

(22) Filed: Dec. 15, 2000

(65) Prior Publication Data

US 2002/0111552 A1 Aug. 15, 2002

Related U.S. Application Data (60) Provisional application No. 60/228,857, filed on Aug. 29, 2000.

(51) Int. Cl.$^7$ ................................................. A61B 8/00
(52) U.S. Cl. ........................ 600/439; 600/443; 600/437
(58) Field of Search ................................. 600/443, 447, 600/437, 439, 445, 448, 459, 456, 458, 432

(56) References Cited

U.S. PATENT DOCUMENTS

| | | | |
|---|---|---|---|
| 4,817,614 A | 4/1989 | Hassler et al. | 128/660.05 |
| 5,052,394 A | 10/1991 | Carpenter et al. | 128/660.06 |
| 5,113,866 A | 5/1992 | Hassler et al. | 128/661.01 |
| 5,381,792 A | 1/1995 | Yanagida et al. | 128/660.03 |
| 5,487,306 A * | 1/1996 | Fortes | 600/443 |
| 5,531,117 A | 7/1996 | Fortes | 73/602 |
| 5,590,657 A | 1/1997 | Cain et al. | 128/660.03 |
| 5,605,154 A * | 2/1997 | Ries et al. | 600/444 |
| 5,752,515 A | 5/1998 | Jolesz et al. | 128/653.1 |
| 6,013,032 A * | 1/2000 | Savord | 128/916 |
| 6,193,663 B1 | 2/2001 | Napolitano et al. | 600/447 |
| 6,419,633 B1 | 7/2002 | Robinson et al. | 600/443 |
| 6,425,867 B1 * | 7/2002 | Vaezy et al. | 600/439 |

FOREIGN PATENT DOCUMENTS

| | | |
|---|---|---|
| WO | WO 98/07373 | 2/1998 |
| WO | WO 99/61903 | 12/1999 |

OTHER PUBLICATIONS

Notification of Transmittal of The International Search Report or the Declaration, mailed Jul. 15, 2002.

Hynynen, et al., "Demonstration of Potential Noninvasive Ultrasound Brain Therapy Through an Intact Skull", Ultrasound in Medicine and Biology, vol. 24, No. 2, pp. 275–283, 1998.

Sun, et al., "Focusing of Therapeutic Ultrasound Through A Human Skull: A Numerical Study", J. Acoust. Soc. Am. 104(3) pt. 1, pp. 1705–1715, Sep. 1998.

Hynynen, Kullervo, "Trans–skull Ultrasound Therapy: The Feasibility of Using Image–Derived Skull Thickness Information to Correct the Phase Distortion", IEEE Trans. on Ultrasonics, Ferroelectrics, and Freq. Control, pp. 752–755, vol. 46, No. 3, May 1999.

Sun, et al., "The Potential of Transskull Ultrasound Therapy and Surgery Using the Maximum Available Skull Surface Area", J. Acoust. Soc. Am. 105(4), pp. 2519–2527, Apr. 1999.

\* cited by examiner

*Primary Examiner*—Francis J. Jaworski
*Assistant Examiner*—Maulin Patel
(74) *Attorney, Agent, or Firm*—Mintz, Levin, Cohn, Ferris, Glovsky and Popeo, P.C.; Ivor R. Elrifi, Esq.; Shane H. Hunter, Esq.

(57) ABSTRACT

The invention provides a method of delivering ultrasound signals. The method includes providing an image of at least a portion of a subject intended to receive ultrasound signals between sources of the ultrasound signals and a desired region of the subject for receiving focused ultrasound signals, identifying, from the image, physical characteristics of different layers of material between the sources and the desired region, and determining at least one of phase corrections and amplitude corrections for the sources depending on respective thicknesses of portions of each of the layers disposed between each source and the desired region.

57 Claims, 5 Drawing Sheets

ULTRASOUND THERAPY

CROSS-REFERENCE TO RELATED APPLICATIONS

This application claims the benefit of U.S. Provisional Application No. 60/228,857, filed Aug. 29, 2000, and entitled "ULTRASOUND THERAPY".

FIELD OF THE INVENTION

The invention relates to medical systems and, more particularly, to non-invasive application of focused ultrasound energy to subjects such as humans, and in particular to the brain of a human subject.

BACKGROUND OF THE INVENTION

Treatment of tissues lying at specific locations within the skull may be limited to removal or ablation. While these treatments have proven effective for certain localized disorders, such as tumors, they involve delicate, time-consuming procedures that may result in destruction of otherwise healthy tissues. These treatments are generally not appropriate for disorders in which diseased tissue is integrated into healthy tissue, except in instances where destruction of the healthy tissue will not unduly effect neurologic function.

The noninvasive nature of ultrasound surgery has special appeal in the brain where it is often desirable to destroy or treat deep tissue volumes without disturbing healthy tissues. Focused ultrasound beams have been used for noninvasive surgery in many other parts of the body. Ultrasound penetrates well through soft tissues and, due to the short wavelengths (1.5 mm at 1 MHz), it can be focused to spots with dimensions of a few millimeters. By heating, e.g., using ultrasound, tumorous or cancerous tissue in the abdomen, for example, it is possible to ablate the diseased portions without significant damage to surrounding healthy tissue.

SUMMARY OF THE INVENTION

In general, in one aspect, the invention provides a method of delivering ultrasound signals. The method includes providing an image of at least a portion of a subject intended to receive ultrasound signals between sources of the ultrasound signals and a desired region of the subject for receiving focused ultrasound signals, identifying, from the image, physical characteristics of different layers of material between the sources and the desired region, and determining at least one of phase corrections and amplitude corrections for the sources depending on respective thicknesses of portions of each of the layers disposed between each source and the desired region.

Implementations of the invention may include one or more of the following features. The physical characteristics are associated with material type and at least one of material density and material structure, the identifying further comprising identifying thicknesses of the layers. The phase corrections are determined in accordance with propagation characteristics of each of the layers. The propagation characteristics are determined based upon the material type and at least one of the material density and the material structure of each of the respective layers. The layers are identified using values associated with portions of the image. The values are intensities of the portions of the image. The phase corrections are determined using a three-layer model of a skull of the subject. Two of the three layers are assumed to have approximately identical speeds of sound, $c_i$, therein, with the other layer having a speed of sound $c_{ii}$ therein, wherein the phase corrections are determined using a phase shift determined according to:

$$\phi = 360 f \sum_{n=1}^{3} D_n \left( \frac{1}{c_0} - \frac{1}{c_n} \right)$$

where $c_n$ is a speed of sound in the $n^{th}$ layer, and $D_n$ is a thickness of the $n^{th}$ layer, and wherein the speeds of sound in the layers are determined according to:

$$c_i(\rho) = (d_1 + d_3) \left[ \frac{d_1 + d_2 + d_3}{c_0} - \frac{d_2}{c_{ii}} - \frac{\phi(\rho)}{360 f D} \right]^{-1}$$

where $d_1$, $d_2$, $d_3$, are thicknesses of the three layers, $\phi(\rho)$ is a measured phase shift as a function of density, and $\rho$ is density.

Further, implementations of the invention may include one or more of the following features. The physical characteristics are associated with x-ray attenuation coefficients, $\mu$. The material between the sources and the desired region is bone. The phase corrections are related to the attenuation coefficient by a phase function including parameters derived at least partially experimentally. Each phase correction equals $M + B\Sigma(1/\mu(x)) + C\Sigma(1/\mu(x))^2$, where $\mu(x)$ is the attenuation coefficient as a function of distance x along a line of propagation between each source and the desired region, and where M, B, and C are derived at least partially experimentally. The amplitude corrections are related to the attenuation coefficient by an amplitude function including parameters derived at least partially experimentally. Each amplitude correction is related to $N + F\Sigma\mu(x) + G\Sigma(\mu(x))^2$, where $\mu(x)$ is the attenuation coefficient as a function of distance x along a line of propagation between each source and the desired region, and where N, F, and G are derived at least partially experimentally.

Further, implementations of the invention may include one or more of the following features. The layers are identified according to both material density and material structure. Providing the image includes producing the image using magnetic resonance imaging. Providing the image includes producing the image using computer tomography. The sources are piezoelectric transducer elements. Both phase and amplitude corrections are determined.

In general, in another aspect, the invention provides a system for delivering ultrasound signals. The system includes an apparatus configured to analyze an image of at least a portion of a subject intended to receive ultrasound signals between sources of the ultrasound signals and a desired region of the subject for receiving focused ultrasound signals, the apparatus configured to determine, from the image, information about different layers of the at least a portion of the subject, and an array of sources of ultrasound signals having at least one of their relative phases and their amplitudes set in accordance with the information about each layer of the at least a portion of the subject provided by the apparatus.

Implementations of the invention may include one or more of the following features. The phases are set in accordance with propagation characteristics of each layer of the at least a portion of the subject. The propagation characteristics are dependent upon the material type and at least one of the material density and the material structure of each layer of the at least a portion of the subject. The apparatus is configured to identify the layers using values associated with portions of the image. The values are intensities of the portions of the image. The apparatus is configured to determine the information about different layers of bone. The apparatus is configured to determine the phase corrections using a three-layer model of a skull of the subject. The information is associated with an x-ray attenuation coefficient, $\mu$. The phase corrections are related to the attenuation coefficient by a phase function including parameters derived at least partially experimentally. The amplitude corrections are related to the attenuation coefficient by an amplitude function including parameters derived at least partially experimentally.

Further, implementations of the invention may include one or more of the following features. The system further includes a magnetic resonance imager coupled to the apparatus and configured to produce the image. The system further includes a computer tomography imager coupled to the apparatus and configured to produce the image. The sources are piezoelectric transducer elements.

In general, in another aspect, the invention provides a computer program product residing on a computer readable medium and comprising instructions for causing a computer to analyze an image of at least a portion of a subject to receive ultrasound signals between sources of the ultrasound signals and a desired region of the subject for receiving focused ultrasound signals to identify, from the image, physical characteristics of layers of material between the sources and the desired region, and to determine at least one of phase corrections and amplitude corrections for the sources depending on respective thicknesses of portions of each of the layers disposed between each source and the desired region.

Implementations of the invention may include one or more of the following features. The phase corrections are determined in accordance with propagation characteristics of each of the layers. The propagation characteristics are dependent upon the material type and at least one of the material density and the material structure of each of the respective layers. The layers are identified according to both material density and material structure. The computer program product further includes instructions for causing a computer to produce the image using magnetic resonance imaging. The computer program product further includes instructions for causing a computer to produce the image using computer tomography. The instructions for causing a computer to identify layers of materials are for causing the computer to identify the layers of materials based upon intensities of portions of the image.

Further, implementations of the invention may include one or more of the following features. The layers are identified using values associated with portions of the image. The values are intensities of the portions of the image. The layers analyzed are layers of bone. The phase corrections are determined using a three-layer model of a skull of the subject. Two of the three layers are assumed to have approximately the same speed of sound, $c_i$, therein, with the other layer having a speed of sound $c_{ii}$ therein, wherein the phase corrections are determined using a phase shift determined according to:

$$\phi = 360f \sum_{n=1}^{3} D_n \left( \frac{1}{c_0} - \frac{1}{c_n} \right)$$

where $c_n$ is a speed of sound in the $n^{th}$ layer, and $D_n$ is a thickness of the $n^{th}$ layer, and wherein the speeds of sound in the layers are determined according to:

$$c_i(\rho) = (d_1 + d_3)\left[ \frac{d_1 + d_2 + d_3}{c_0} - \frac{d_2}{c_{ii}} - \frac{\phi(\rho)}{360fD} \right]^{-1}$$

where $d_1$, $d_2$, $d_3$, are thicknesses of the three layers, $\phi(\rho)$ is a measured phase shift as a function of density, and $\rho$ is density.

Further, implementations of the invention may include one or more of the following features. The physical characteristics are associated with x-ray attenuation coefficients, $\mu$. The phase corrections are related to the attenuation coefficient by a phase function including parameters derived at least partially experimentally. Each phase correction equals $M+B\Sigma(1/\mu(x))+C\Sigma(1/\mu(x))^2$, where $\mu(x)$ is the attenuation coefficient as a function of distance x along a line of propagation between each source and the desired region, and where M, B, and C are derived at least partially experimentally. The amplitude corrections are related to the attenuation coefficient by an amplitude function including parameters derived at least partially experimentally. Each amplitude correction is related to $N+F\Sigma\mu(x)+G\Sigma(\mu(x))^2$, where $\mu(x)$ is the attenuation coefficient as a function of distance x along a line of propagation between each source and the desired region, and where N, F, and G are derived at least partially experimentally.

In general, in another aspect, the invention provides a method of providing ultrasound signals into a subject from at least one source of an array of sources of ultrasound signals. The method includes (a) transmitting ultrasound energy of a selected frequency from a selected source into the subject, (b) receiving superimposed reflections of the transmitted energy, the reflections being from an outer surface of the subject and at least one interface inside the subject, (c) repeating (a) and (b) using ultrasound energy of frequencies other than the selected frequency, (d) determining a frequency difference between frequencies associated with relative extrema of the received reflections, and (e) using the determined frequency difference and a thickness, of at least a portion of material between the selected source and a desired region in the subject for receiving focused ultrasound energy signals, to determine a phase correction for the selected source.

Implementations of the invention may include one or more of the following features. The method further includes (f) providing an image of at least a portion of a subject intended to receive ultrasound energy signals between sources of the energy signals and the desired region, and (g) identifying, from the image, the thickness of at least a portion of material between the selected source and the desired region. The method further includes repeating (a)–(e) for each of the sources other than the selected source. The phase correction is determined according to:

$$\Delta\phi = 2\pi f[(d/c_0) - (1/(2\Delta f))]$$

where $\Delta\phi$ is the phase correction, f is a frequency to be transmitted, d is the thickness, $c_0$ is the speed of sound in water, and $\Delta f$ is the frequency difference between like extrema.

In general, in another aspect, the invention provides logic for use in a system for providing ultrasound energy into a living subject from an array of sources of ultrasound energy signals. The logic is configured to control apparatus to (a) transmit ultrasound energy of a selected frequency from a selected source into the subject, (b) receive superimposed reflections of the transmitted energy, the reflections being from an outer surface of the subject and at least one interface inside the subject, (c) repeat (a) and (b) using ultrasound energy of frequencies other than the selected frequency, (d) determine a frequency difference between frequencies associated with relative extrema of the received reflections, and (e) use the determined frequency difference and a thickness, of at least a portion of material between the selected source and a desired region in the subject for receiving focused ultrasound energy signals, to determine a phase correction for the selected source.

Implementations of the invention may include one or more of the following features. The logic is further configured to cause the apparatus to (f) provide an image of at least a portion of a subject intended to receive ultrasound energy signals between sources of the energy signals and the desired region, and (g) identify, from the image, the thickness of at least a portion of material between the selected source and the desired region. The logic is further configured to cause the apparatus to repeat (a)–(e) for each of the sources other than the selected source. The logic is configured to cause the apparatus to determine the phase correction according to:

$$\Delta\phi = 2\pi f[(d/c_0) - (1/(2\Delta f))]$$

where $\Delta\phi$ is the phase correction, f is a frequency to be transmitted, d is the thickness, $c_0$ is the speed of sound in water, and $\Delta f$ is the frequency difference between like extrema.

Various aspects of the invention may provide one or more of the following advantages. Ultrasound can be focused accurately within an intact skull, e.g., for ultrasound therapy. Different skulls, e.g., different skull thicknesses, densities, and/or structures, can be accommodated for ultrasound therapy. Real-time adjustments to ultrasound therapy can be made. Effects on phase and/or amplitude of energy passing through bone (or other tissue) may be determined and used to compensate the phase and/or amplitude of energy applied to the bone (or other tissue).

These and other advantages of the invention, along with the invention itself, will be more fully understood after a review of the following figures, detailed description, and claims.

DETAILED DESCRIPTION OF PREFERRED EMBODIMENTS

Energy, such as ultrasound energy, may be propagated into a subject such as a human or animal, for various therapeutic reasons. Arrays of radiating transducer elements may be used to transmit energy into the subject, and the amplitudes of the signals transmitted by the elements can affect how much energy penetrates the subject and the relative phases and amplitudes of energies transmitted can help to focus a distribution of energy in the subject. It has been found that the phases and amplitudes of ultrasound signals may be affected/distorted by many causes such as different material properties of materials through which the signals are propagated. For example, different types of materials within a patient, e.g., bone, muscle, and fat, have different propagation and attenuation constants of ultrasound energy. Also, other material properties, such as the density and structure of materials in a patient, may affect the phase and/or attenuation of ultrasound signals. Because the signals from different transducer elements may encounter different thicknesses and contours of materials and possibly air-filled or liquid-filled pockets between transducer elements and a region to be imaged/treated, the phases of the signals from the transducer elements will often be distorted. The resulting phases and/or amplitudes will therefore often be different than desired if the transmission phases and/or amplitudes are not compensated for this distortion.

Embodiments of the invention provide techniques for compensating for phase distortions and attenuation variances when treating a patient using ultrasound. Using imaging techniques such as computer tomography (CT), magnetic resonance imaging (MRI), etc., properties such as thickness, density, and structure of materials are determined. It has been discovered that each of these properties affects the phase distortion of materials, so that phase corrections determined using all three properties will be better than those determined using only one or two of the properties. The determined properties for materials in a subject between transducer elements and a region to be treated are inserted into formulas developed by the inventors. The formulas use the determined properties and known characteristics, e.g., propagation speed, to calculate phase adjustments for each of the transducer elements. Compensating the phase in the transducer elements more properly focuses energy within the subject, permitting effective noninvasive therapy, even in sensitive areas such as the brain. Also, x-ray attenuation can be related to phase distortion and acoustic attenuation. Formulas relating to x-ray attenuation to phase distortion and acoustic attenuation can be used to compensate for such variances by adjusting transmitted phase and amplitude accordingly.

Figure 1:
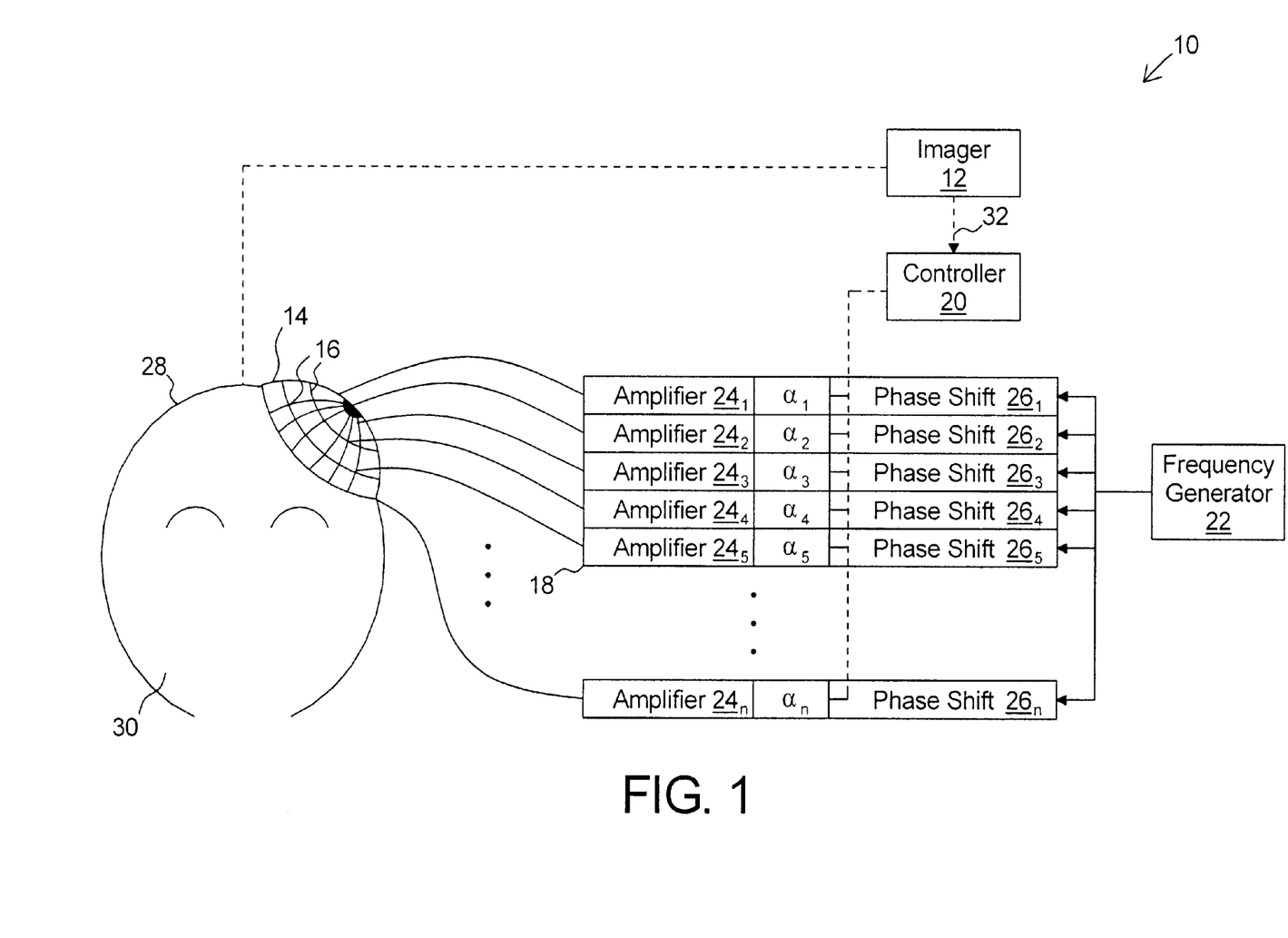
FIG. 1 is a schematic diagram of an ultrasound therapy system according to the invention.

Referring to FIG. 1, an ultrasound therapy system 10 includes an imager 12, a phased array 14 of n transducer elements 16, a signal adjuster 18, a controller 20, and a frequency generator 22. The system 10 is configured to determine characteristics of a skull 28 of a patient 30, and to apply ultrasound energy (e.g., in the range 0.01 MHz to 10 MHz) that is focused in the patient's brain. Signals to the array are provided by a driving arrangement similar to that reported in Daum et al., "Design and Evaluation of a Feedback Based Phased Array System for Ultrasound Surgery." IEEE Trans. Ultrason. Ferroelectr. Freq. Control 45(2):431–4, 1998, but with a driving frequency selected between about 0.1 MHz and about 10 MHz. The power and phase to each transducer element 16 may be manually controlled or automatically controlled using software and feedback.

The array 14 of transducer elements 16 is configured to be disposed on or near the external surface of the patient's skull 28. The array 14 is configured in a curved shape (e.g., spherical, although sections of other shapes are possible such as planar) conducive for being placed on the patient's head and for focusing ultrasound energy at a distance from the surface of the array 14. The transducer elements 16 of the array 14 are piezoelectric transducer elements arranged in the array 14 as shown. The transducer elements (e.g., 1 cm² piezoelectric ceramic pieces) are mounted in silicone rubber or any other material suitable for damping the mechanical coupling between the elements 16. Other materials may also be used for the array construction. For example, the array 14 may be formed from one or more pieces of piezocomposite material, or any material that converts electrical energy to acoustic energy. To help assure maximum power transfer to the transducer elements 16, the transducer elements 16 may be configured for electrical resonance at 50Ω to help match input connector impedance.

The array 14 is coupled to the signal adjuster 18 that is further coupled to the frequency generator 22. The frequency generator 22 is configured to provide a common radio frequency (RF) signal as the input signal to the signal adjuster 18. The radio frequency generator 22 can be of any type that will produce the appropriate signals for the signal adjuster 18. For example, the generator 22 may be a Model DS345 generator available from Stanford Research Systems. Together, the radio frequency generator 22 and signal adjuster 18 are configured to drive the individual transducer elements 16 of the array 14 at the same frequency, but at different phases (and possibly different amplitudes), in order to transmit ultrasound energy through the patient's skull 28 and focus the energy at a selected region within the patient's brain. The generator 22 is coupled to the adjuster 18 to split the generator's output signal to provide n input signals to the signal adjuster 18.

Coupled to receive each of the n input signals from the frequency generator 22 are n pairs of amplifiers $24_1$–$24_n$ and associated phase shifters $26_1$–$26_n$ of the signal adjuster 18. Each pair of phase shifter 26 and amplifier 24 represents a channel of the signal adjuster 18. The phase shifters 26 are configured to provide n independent output signals to the amplifiers 24 by altering or adjusting the phase (and possibly amplitude) of the incoming signals from the generator 22 by respective phase shift factors $\alpha_1$–$\alpha_n$. The phase shifters 26 provide approximately 1 degree precision (8-bit resolution, although lower phase resolution may be adequate for many applications). The amplifiers $24_1$–$24_n$ are configured to amplify the signals from the phase shifters 26 and to provide the amplified signals to the transducer elements 16 through connections, e.g., coaxial cables, individually connecting the amplifiers 24 and the transducer elements 16. An internal power meter is configured to monitor power supplied by the amplifiers 24.

The phase shift factors $\alpha_1$–$\alpha_n$ of the phase shifters 26 provide steering of the ultrasound beam absent an object in the path of the ultrasound energy and also provide compensation for phase distortion in the ultrasound output by each transducer element 16 induced by the patient's skull. The component of each phase shift factor associated with steering can be computed using known techniques. The component of each phase shift factor $\alpha_1$–$\alpha_n$ associated with phase distortion compensates for perturbations and distortions introduced by the skull 28, the skin/skull interface, the dura matter/skull interface, by variations in the skull thickness and by structural considerations such as air-filled or liquid-filled pockets in the skull 28. The two components that make up the phase shift factors $\alpha_1$–$\alpha_n$ are summed in order to determine the composite phase shift factors $\alpha_1$–$\alpha_n$ for the respective channels in order to focus ultrasound energy at a desired steering angle relative to, and distance from, the array 14.

The phase shift factors $\alpha_1$–$\alpha_n$ are provided by the controller 20. The controller 20 is logic that may be provided by software, hardware, firmware, hardwiring, or combinations of any of these. For example, the controller 20 can be a general purpose, or special purpose, digital data processor programmed with software in a conventional manner in order to provide and apply the phase shift factors $\alpha_1$–$\alpha_n$ to the phase shifters 26, although other configurations may be used. The controller 20 is configured to determine the phase shift factors $\alpha_1$–$\alpha_n$ as described below based on information obtained from the imager 12 as indicated by arrow 32. In particular, the information includes the thickness and density of the patient's skull 28 for each portion of the skull 28 between each transducer element 16 and the desired focal point in the patient's brain. Information from the imager 12 is conveyed directly from the imager 12 because the imager 12 is configured to automatically analyze images and determine characteristics of interest from the images. Enough information is provided by the imager 12 to the controller 20 to determine the phase shift factors $\alpha_1$–$\alpha_n$.

The controller 20 is configured to manipulate images from the imager 12. The controller 20 is configured to produce a 3-dimensional rendering of the patient's skull 28 from 2-dimensional images received from the imager 12 and to determine skull thickness from the 3-dimensional rendering. The 3-dimensional rendering can be divided by the controller 20 into voxels (a volume pixel of the 3-dimensional image).

The imager 12 is configured to obtain images of the interior of the patient's head, and in particular images that provide information regarding thickness, density, and structure of bone of the patient's skull 28. For example, the imager 12 may be a Magnetic Resonance Imaging (MRI) device or Computer Tomography (CT) device. The imager 12 is configured to scan the patient's skull 28 and provide information related to skull thickness, density and structure. This information includes 2-dimensional images of varying intensity from which 3-dimensional renderings can be made and from which thicknesses and densities can be determined and/or inferred. Three-dimensional image acquisition may also be possible and can be used. Also, if the imager 12 is a CT device, the imager 12 can determine and provide the CT number (also called Hounsfield number) for each pixel in images provided by the imager 12.

Figure 2:
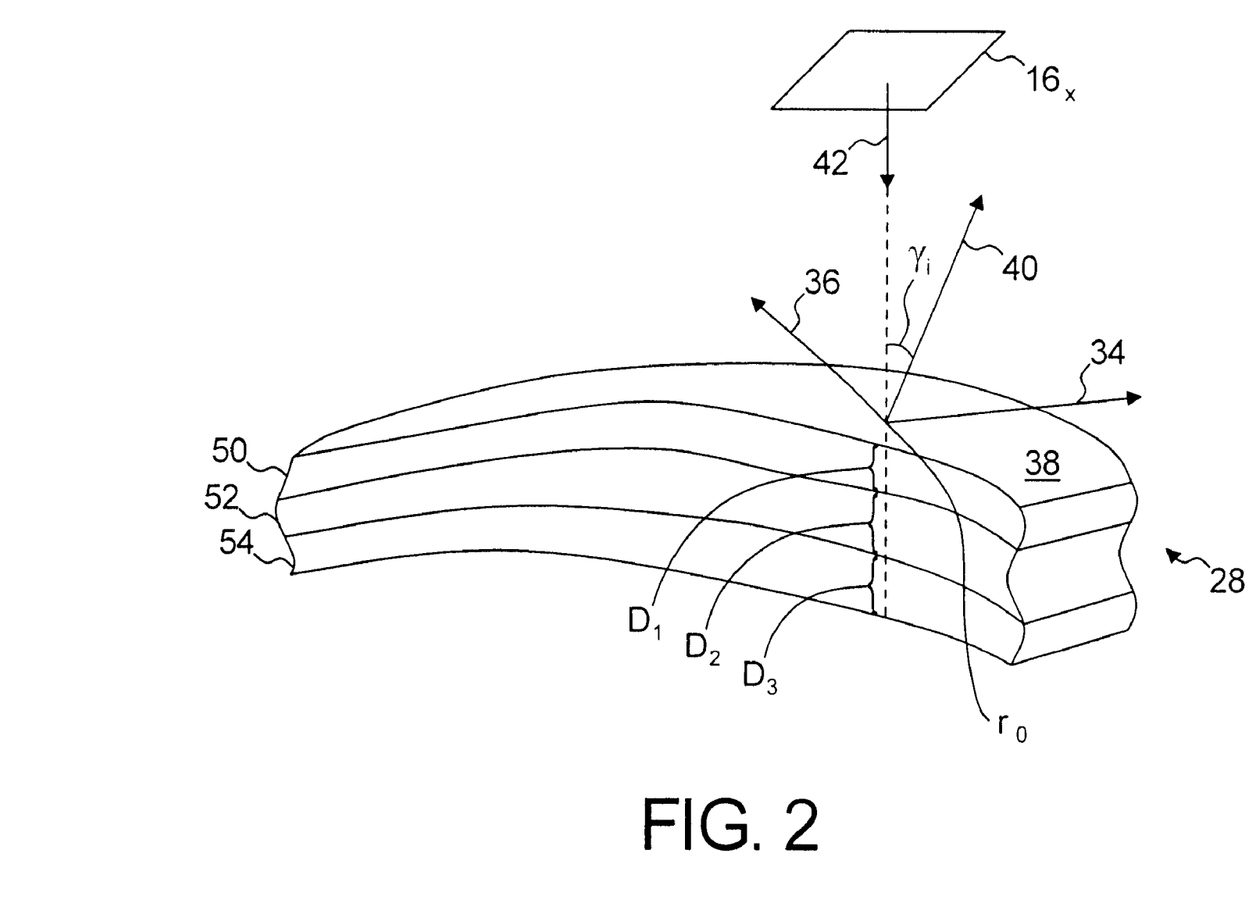
FIG. 2 is a 3-dimensional rendering of a portion of a patient's skull.

Referring also to FIG. 2, the skull 28 includes two layers 50, 54 of trabecular bone and a layer 52 of cortical bone. For reference, a scan direction of the imager 12 is defined as the Cartesian x-axis so that the image plane is defined by the y-axis and z-axis. From the 3-D rendering, two vectors 34, 36 on the surface 38 of the skull 28 are determined using the $3^{rd}$ nearest neighboring points on the surface in the x and y directions from the point of interest $r_0$ on the skull's surface 38. The controller 20 is configured to use the vectors 34, 36 to calculate a vector 40 that is normal to the surface 38. The controller can calculate a scalar product of the vector 40 and a vector 42 that is the direction of propagation of energy from a transducer element $16_x$. This scalar product is the incident angle:

$$\gamma_i = \cos^{-1}\left[\frac{-(\alpha_1 \times \alpha_2) \cdot \beta}{|(\alpha_1 \times \alpha)||\beta|}\right]. \quad (1)$$

A Cartesian (normalized) unit vector n=(u,v,w) may be calculated by the controller 20 from this incident angle $\gamma_i$. Thicknesses, $D_1$, $D_2$, $D_3$, of each layer 50, 52, 54, respectively, are obtained, using intensity variations, starting at a location on the skull surface $r_0=(x_0,y_0,z_0)$ and continuing to a point on the next layer r=(x,y,z), $$r=r_0+D\,n. \quad (2)$$

Near-normal propagation through homogeneous skull bone is assumed. Treating the layers 50, 52, 54 as a single layer for purposes of ultrasound propagation speed, the following simple relation can be used to express the phase shift due to propagation through a given point on the skull.

$$\phi = 360 fD \left( \frac{1}{c_0} - \frac{1}{c_s} \right) \quad (3)$$

where f is the driving frequency, the sound speed in water is $c_0$, the speed in the skull bone is $c_s$, and D is the thickness of the skull. This convention of subtracting the phase shift due to direct propagation of the field in water from the shift due to the skull produces a positive phase shift.

The three layers 50, 52, 54 can be treated separately to determine phase compensation due to the thicknesses $D_1$, $D_2$, $D_3$ of the layers 50, 52, 54 as part of a three-layer model. For the three-layer model, it has been assumed that the skull 28 consists of individual homogeneous layers. The speed of sound is assumed to be $2.5 \times 10^3$ m/s for the central layer 52 and $2.9 \times 10^3$ m/s for the inner and outer layers 50, 54. The expected phase shift across the skull 28 using this three-layer model is:

$$\phi = 360 f \sum_{n=1}^{3} D_n \left( \frac{1}{c_0} - \frac{1}{c_n} \right) \quad (4)$$

with $c_n$ equal to the speed of sound in the $n^{th}$ layer and $D_n$ being the thickness of the $n^{th}$ layer.

It has been found that density of the skull 28 affects the propagation through the skull 28. Consequently, the phase of ultrasound signals passing through the skull 28 is affected by the skull's density, and phase correction based on the skull's density can help improve focusing of ultrasound energy from the array 14.

To assess the contribution of internal density variation to the deviation from the expected single-layer homogeneous values calculated from Eq. (3), a correlation between the mean CT image intensity along the ultrasound axis of propagation 42 and experimental error is used. Using a 3-d image constructed from 2-d CT images, each 0.15 mm² voxel is assigned an intensity value. It is assumed that the intensity is linearly proportional to bone density and density is scaled to MKS units using air and water in the image as reference intensities. Mean intensity is determined by summing the CT intensity values along the axis of propagation 42 inside the bone and dividing by the total number summed of voxels. The voxels may include air-filled or liquid-filled pockets. The sound speed for such voxels is assumed to be the speed of sound in water, or if air-filled, then complete reflection of the ultrasound can be assumed.

Error due to skull density has been calculated as the difference between the measured phase and that given by Eq. (3) (for a single-layer model). An empirical correction factor has been obtained by fitting (using a polynomial curve fit) percent error as a function of the mean intensity. The correction factor is:

$$C(\rho) = \sum_{n=0}^{N} A_n \rho^{N-n} \quad (5)$$

where there are N+1 coefficients $A_n$ to be determined for an $N^{th}$ degree fit, and $\rho$ is the density. Applying a $3^{rd}$ order fit using a 117 point data set and five skulls at 0.51 MHz yielded coefficients, in MKS units, of:

TABLE 1

| | |
|---|---|
| $A_0$ | 1.1424e-008 |
| $A_1$ | -7.5377e-005 |
| $A_2$ | 0.1645 |
| $A_3$ | -118.689 |

These coefficients may be used in Eq. (5), and Eq. (5) applied to Eq. (3) as part of the single-layer homogeneous model to yield a corrected phase shift of:

$$\phi = \frac{\Phi}{1+C}, \quad (6)$$

where $\Phi$ contains the initial phase values obtained using Eq (3).

The density and thickness measurements may also be applied toward adjustment of the skull sound speed. To adjust the speed value for a single layer, the controller 20 is configured to fit the speed as a function of density according to:

$$c_s(\rho) = \left[ \frac{1}{c_0} - \frac{\phi(\rho)}{360 fD} \right]^{-1} \quad (7)$$

where $\phi(\rho)$ is the measured phase shift as a function of density. A polynomial fit as shown in Eq. (5) is used by the controller 20 to find the speed of sound values. For the three layer model, two sound speeds are calculated. These two speeds are the speed $c_i$ for the trabecular layers and the speed $c_{ii}$ of the cortical (central) bone. Given the thicknesses $D_1$, $D_2$, and $D_3$, respectively, for the three bone layers 50, 52, 54, the speed $c_{ii}$ of the cortical layer is fit by the controller 20 as a function of density according to:

$$c_i(\rho) = (d_1 + d_3) \left[ \frac{d_1 + d_2 + d_3}{c_0} - \frac{d_2}{c_{ii}} - \frac{\phi(\rho)}{360 fD} \right]^{-1}. \quad (8)$$

The polynomial fit for $c_i(\rho)$ is performed using Eq. (5) over a series of trial functions for $c_{ii}$. The final sound speeds are the $c_i(\rho)$ and $c_{ii}(\rho)$ that most closely correlate by standard deviation or other methods with direct skull measurements obtained by fitting a large skull sample.

Figure 3:
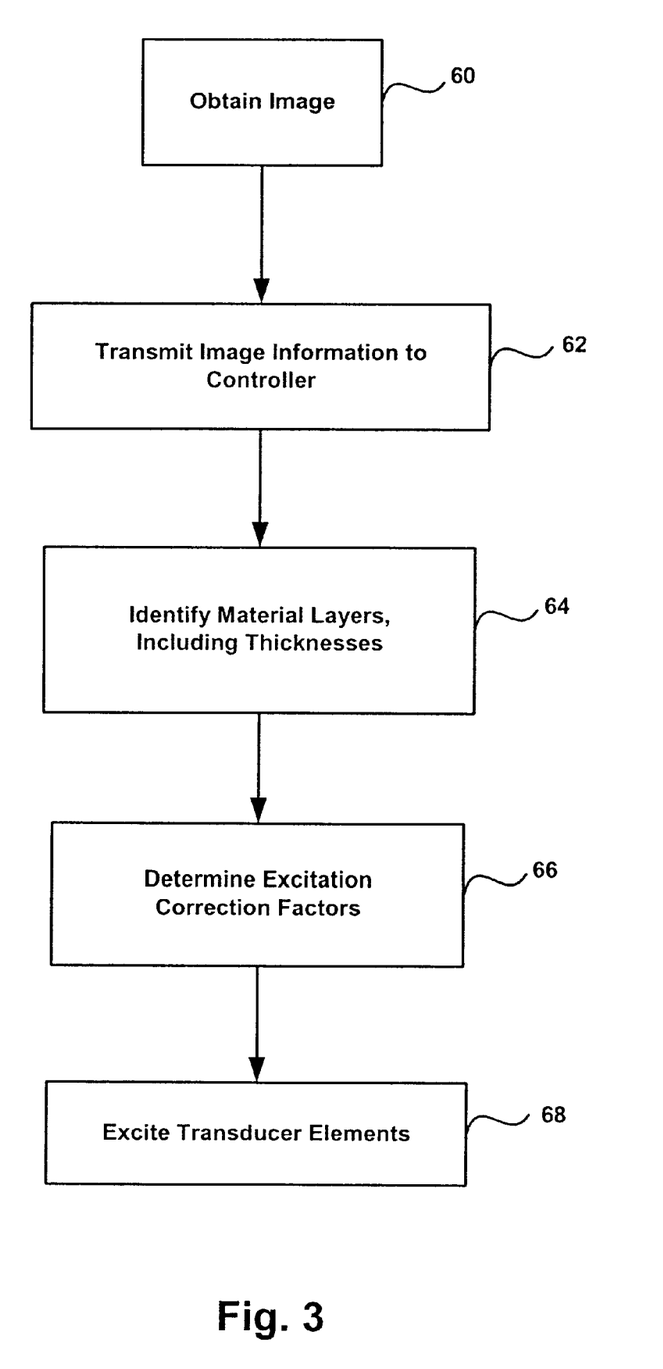
FIG. 3 is a flow diagram of a process of determining excitation correction factors and exciting transducer elements using the determined factors.

Referring to FIGS. 1 and 3, in operation, the controller 20 uses information from the imager 12 to adjust the phase of the transducer elements 16. At stage 60, the imager 12 takes images of the patient's skull 28. This may be done remotely in space, e.g., in another hospital, from the controller 20. At stage 62, the imager transmits information, e.g., intensities of portions of the image, related to skull thickness, density, and structure to the controller 20. This transmission can be separated in time from when the imager 12 takes the image and can also be performed by human intervention, e.g., by recording the images on a CD and replaying the CD in the controller 20. At stage 64, the controller 20 manipulates this information to determine thicknesses of layers, and to identify the layers, of the patient's skull 28 by analyzing intensities of portions of the image. At stage 66, the controller 20 determines excitation correction factors such as the phase shift factors $\alpha_1$–$\alpha_n$ (or amplitude corrections as discussed below) and transmits the phase shift factors $\alpha_1$–$\alpha_n$ to the adjuster 18. At stage 68, the frequency generator supplies energy to the adjuster 18. The adjuster 18 adjusts the phase of the energy from the frequency generator 22 according to the phase shift factors $\alpha_1$–$\alpha_n$ from the controller 20. The adjusted energies are sent to the transducer elements 16 that convert the energies into ultrasound waves and transmit these waves into the patient's skull 28. Images from the imager 12 can be supplied in real time and the amplitude and/or phasing of the energy applied to the patient 30 changed in response to the images.

The power supplied to the patient's skull 28 depends on the type of therapy. For ablation, approximately 2–3 kW for approximately 10 seconds using 64 transducer elements may be used. If more transducer elements 16 are used, then less total power may be used and vice versa. For opening the blood-brain barrier, about 100 times less power than for ablation may be used due to preformed gas bubbles in the area of interest. The ablation power can also be reduced by the preformed gas bubbles. Using bursts of energy has been found to reduce, if not eliminate, affects on phase due to standing waves that may occur if the transducer elements 16 constantly emit energy.

Other embodiments are within the scope and spirit of the appended claims. For example, the array 14 of transducer elements 16 shown in FIG. 1 may contain fewer transducer elements 16 than shown. The phase shift factors $\alpha_1$–$\alpha_n$ may be pre-stored in the channels of signal adjuster 18 instead of being provided by the controller 20. Further, functions described as being performed by the controller 20 could be performed by the imager 12 and vice versa, or by a person using the system 10, e.g., calculating densities and providing input data to the controller 20 regarding phase shift factors $\alpha_1$–$\alpha_n$.

Figure 4:
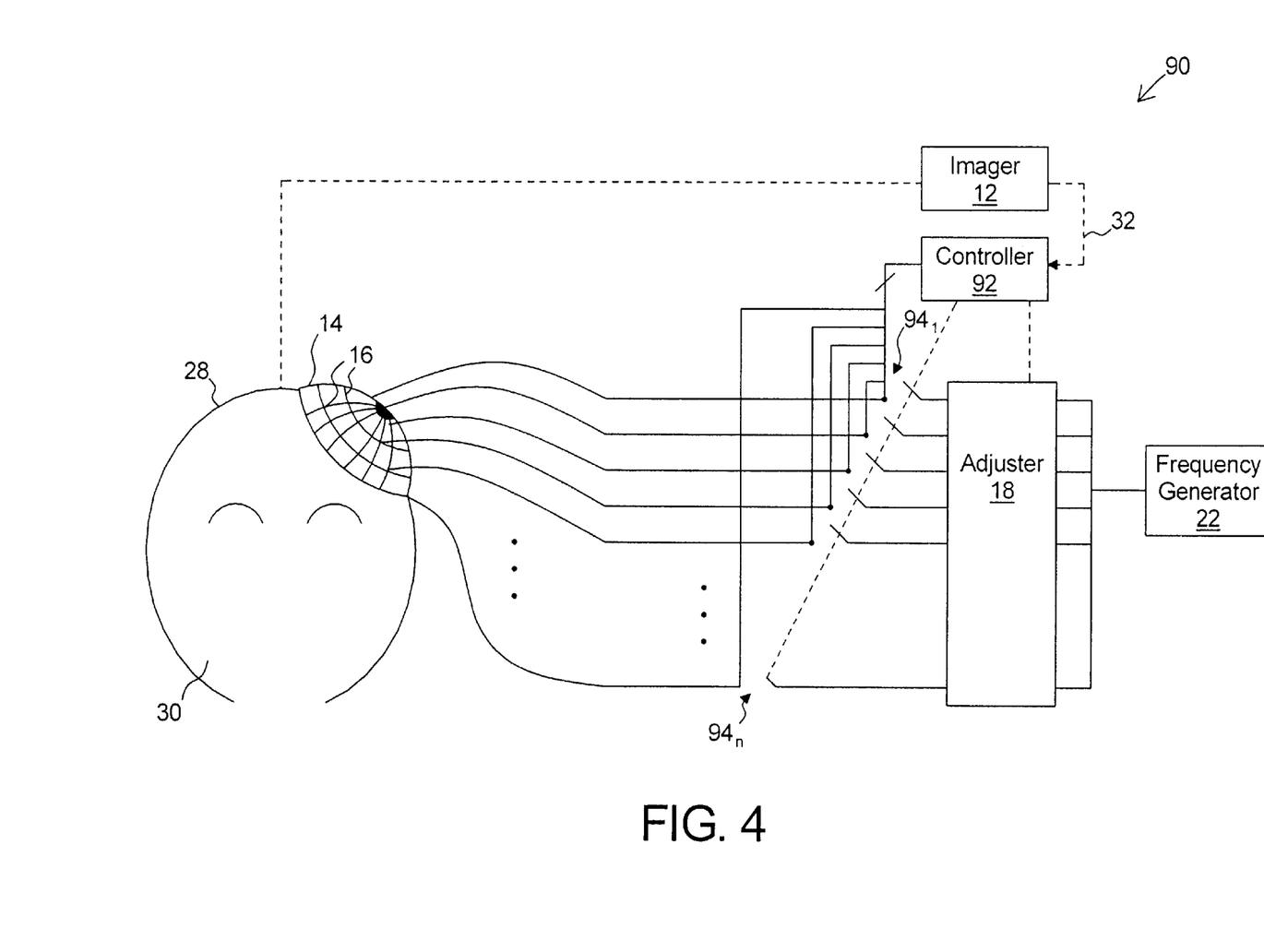
FIG. 4 is a schematic diagram of another ultrasound therapy system according to the invention.
Figure 5:
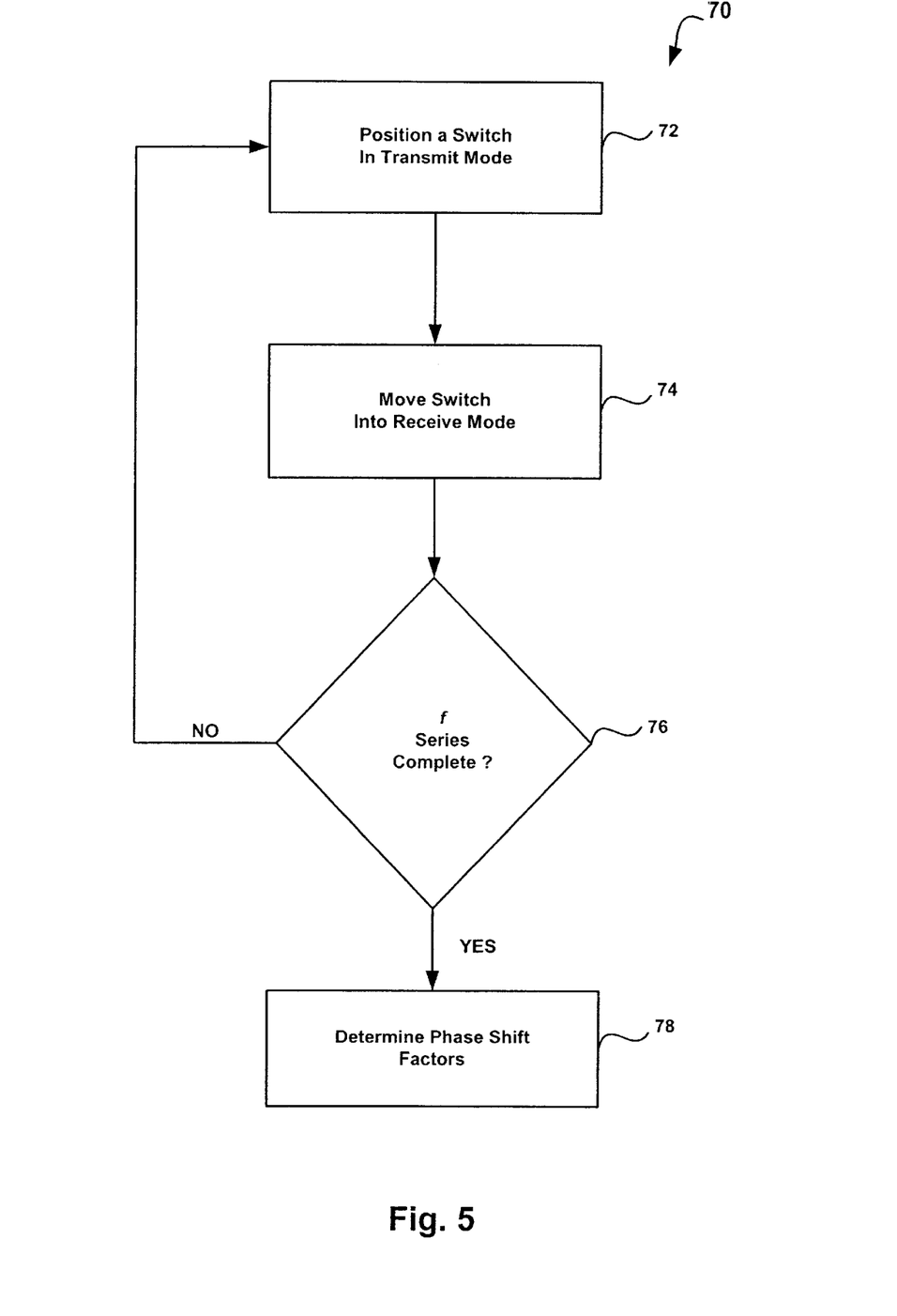
FIG. 5 is a flow diagram of a process of obtaining phase shift factors using the system shown in FIG. 4.

Referring to FIGS. 4–5, a noninvasive process 70 for obtaining phase shift factors $\alpha_1$–$\alpha_n$ using a system 90 operates the transducer elements 16 in both transmit and receive modes. In the system 90, a controller 92 is similar to the controller 20 (FIG. 1), but is also configured to control switches $94_1$–$94_n$ such that the transducer elements 16 are connected to the controller 92 in a receive mode and to the adjuster 18 in a transmit mode.

At stage 72, the controller 92 controls the switches 94 to be positioned such that one switch, e.g., switch $94_1$, is in the transmit mode. The frequency generator 22 produces a low-frequency ultrasound wave train of about 5–30 cycles. Some of this wave train reflects off of the skull 28 and some of the wave train passes through the skull 28 into the patient's brain.

At stage 74, the controller 92 causes the switch $94_1$ to switch into the receive mode, connecting the transducer element $16_1$ to the controller 92. The wave train reflects off of the skull 28 and reflections are received by the transducer element $16_1$ and recorded by the controller 92. The propagation speeds and the pulse train lengths are such that energy from a pulse train is still being transmitted into, and reflected by, the outer surface of the skull 28 when energy from that pulse train that was reflected by the inner surface of the skull 28 passes through the skull 28 toward the array 14. Thus, the received reflections of the inner and outer surfaces are superimposed.

At stage 76, a query is made as to whether a series of frequencies to be transmitted has been completed. If not, then the process 70 returns to stage 72 to transmit a different frequency in the series. If the series has been completed, with corresponding recorded amplitude data as a function of frequency, then the process 70 proceeds to stage 78.

At stage 78, the controller 92 analyzes and processes the recorded information to determine the phase shift factors $\alpha_1$–$\alpha_n$. The controller 92 deconvolves the recorded frequency response that includes the superimposed reflections from the interfaces at the inner and outer surfaces of the skull. The superimposed reflections produce a periodic appearance of local maxima and minima in the data as a function of frequency. Information from images, e.g., CT or MRI images, are used by the controller 92 to determine the locations of the inner and outer surfaces, and thus the skull thickness. The controller 92 estimates the phase shift ($\Delta\phi$) using the distance, $\Delta f$, between like extrema, e.g., peaks, according to:

$$\Delta\phi = 2\pi f[(d/c_0) - (1/(2\Delta f))] \tag{9}$$

where f is a frequency to be transmitted for which the phase correction is to be used, d is the skull thickness determined from the image, and $c_0$ is the speed of sound in water. Adjustments may be made to this phase shift using density correction techniques. The process 70 is repeated for the remainder of the transducer elements 16.

Phase shifts and acoustic attenuation due to transskull sonication can also be determined from analysis of CT images. For purposes of determining phase shift and acoustic attenuation, it can be assumed that there is essentially a one-to-one correlation between x-ray attenuation coefficient $\mu$ and the speed of sound c in bone and between $\mu$ and acoustic attenuation.

Equations relating x-ray attenuation to phase and acoustic attenuation have been developed as discussed below, with the equations including parameters determined from fitting to experimental data. Experimental data has been determined by applying ultrasound to a pig skull sample using a 1" transducer element made by Panametrics of Waltham, Mass., operating at 730 kHz and positioned about 7 cm from a 0.6 mm hydrophone. The skull was attached to a 3-D positioning system and the transducer element was driven by a 10-cycle sinusoid signal produced by a waveform generator such as a Wavetek model 395 made by Wavetek Ltd. of Norwich, United Kingdom, or a waveform generator made by, e.g., Fluke Corporation of Everett, Wash. The hydrophone response was recorded on an HP54602 digital oscilloscope made by Hewlett Packard of Palo Alto, Calif. Measurements of the skull sample were obtained by immersing the sample in water and using dual-slice spiral acquisition with 0.5 mm slices.

Phase shift through the skull can be related to x-ray attenuation by assuming a formulaic relationship and fitting actual data to the formula. The x-ray attenuation coefficient $\mu$ is related to the CT number $CT_n$ according to:

$$\mu = k(CT_n + 1,000) \tag{10}$$

where k is a well-known physical constant. The units of $\mu$ may be chosen such that k=1. The phase shift due to the passage through the bone is given by:

$$\Delta\phi = 2\pi f \int (1/c(x) - 1/c_0) dx \tag{11}$$

where f is the frequency, c(x) is the speed of sound at point x and $c_0$ the speed of sound in water (or soft tissue, that is practically the same). The integration in Eq. 11 is performed along the line of propagation of the ultrasound energy. The functional dependence on $\mu$ is assumed to be:

$$1/c(x) = A' + B'(1/\mu(x)) + C'(1/\mu(x))^2 \tag{12}$$

where A', B' and C' are parameters fitted to the experimental data determined from experiments using the setup described above. Approximations other than that shown in Eq. 12 may be used. From Eqs. 11 and 12:

$$\Delta\phi = A(p_2 - p_1 + 1) + B\Sigma(1/\mu(x)) + C\Sigma(1/\mu(x))^2 \tag{13}$$

where $A=2\pi f(A'-1/c_0)$, $B=2\pi fB'$, $C=2\pi fC'$, and $p_2$, $p_1$ are the first within the bone along the line of propagation and the sums are performed within these boundaries. The values of $p_2$, $p_1$ are obtained manually from intensity profiles drawn along the lines of propagation. These values may also be obtained automatically using well-known edge-detection techniques.

The equation for $\Delta\phi$ can be modified to include a thickness-independent parameter. Thus, Eq. 13 can be modified to:

$$\Delta\phi = A(p_2-p_1+1) + B\Sigma(1/\mu(x)) + C\Sigma(1/\mu(x))^2 + J \quad (14)$$

where J is the phase shift at zero thickness and its non-zero value is probably due to experimental error. The value of $\Delta\phi$ can be used to adjust the phases of elements of an array of transducer elements such as the array 14 of the system 10 shown in FIG. 1.

From experiments using the setup described above, exemplary values of the parameters A, B, C, and J were obtained. These values were $A=0.1126$, $B=-0.0610$, $C=-0.0759$, and $J=-0.1375$. Using these values in Eq. 14 yielded superior results (e.g., a standard deviation of 21°) when compared to $$\Delta\phi = 2\pi f x/(1/c_b - 1/c_0)$$

and assuming $c_b=2650$ m/sec and $c_0=1500$ m/sec (e.g., a standard deviation of 54°).

Acoustic attenuation through the skull can also be related to x-ray attenuation by assuming a formulaic relationship and fitting actual data to the formula. The acoustic attenuation through bone is given by:

$$\ln(I/I_0) = -\int \mu_{AC}(x)dx \quad (15)$$

Where I and $I_0$ are the acoustic intensities before and after the passage through the bone respectively and $\mu_{AC}(x)$ is the local acoustic attenuation coefficient. The relation between the acoustic and x-ray attenuation coefficients can be approximated as:

$$\mu_{AC}(x) = E + F\mu(x) + G(\mu(x))^2 \quad (16)$$

Approximations other than that shown in Eq. 16 may also be used. Integrating over the set of pixels along the line of propagation, as explained above, yields:

$$-\ln(I/I_0) = E(p_2-p_1+1) + F\Sigma\mu(x) + G\Sigma(\mu(x))^2 + H \quad (17)$$

where H is a thickness-independent parameter that reflects the fraction of the intensity reflected at the interfaces (air-to-skull, between skull layers, and skull-to-brain). Again, parameters E, F, G, and H were determined to be $E=0.7552$, $F=-0.9007$, $G=0.2946$, and $H=-0.9121$. Using information about the acoustic attenuation, the magnitude of transmitted energy can be adjusted using the amplifiers 24 based on signals from the controller 20.

In operation, the imager 12 supplies the CT numbers of images to the controller 20 that uses the CT numbers and the experimentally-determined values for A, B, C, J, E, F, G, & H to determine the phase correction factors $\alpha_1-\alpha_n$ and amplitude adjustment factors for the amplifiers 24. The system otherwise operates generally as described above, with the adjuster 18 adjusting phase and amplitude of energy from the generator 22 as indicated by the controller 20.

Still further embodiments are within the scope and spirit of the appended claims. For example, while the above discussion focused on ultrasound energy transmitted through human skulls, other frequencies of energy and other subjects may be used, and other areas of subjects may be targeted for receiving energy. For example, non-human subjects are acceptable, as well as transmitting energy into areas of human or non-human subjects aside from through the skull and into the brain. Also, other techniques for determining and/or controlling the phase and amplitude of signals transmitted into the patient 30 may be used. For example, techniques that may be used include those of concurrently-filed U.S. patent application Ser. No. 09/724, 817, filed Nov. 28, 2000; entitled "SYSTEMS AND METHODS FOR FOCUSSING AN ACOUSTIC ENERGY BEAM TRANSMITTED THROUGH A SKULL," and concurrently-filed U.S. patent application Ser. No. 09/724, 611, filed Nov. 28, 2000; entitled "SYSTEMS AND METHODS FOR CONTROLLING A PHASED ARRAY FOCUSED ULTRASOUND SYSTEM," both of which are incorporated here by reference.

What is claimed is:

1. A method of delivering ultrasound signals, the method comprising:

providing an image of at least a portion of a subject intended to receive ultrasound signals between sources of the ultrasound signals and a desired region of the subject for receiving focused ultrasound signals;

identifying, from the image, physical characteristics of different layers of material between the sources and the desired region; and determining at least one of phase corrections and amplitude corrections for the sources depending on respective thicknesses of portions of each of the layers disposed between each source and the desired region.

2. The method of claim 1 wherein the physical characteristics are associated with material type and at least one of material density and material structure, the identifying further comprising identifying thicknesses of the layers.

3. The method of claim 2 wherein the phase corrections are determined in accordance with propagation characteristics of each of the layers.

4. The method of claim 3 wherein the propagation characteristics are determined based upon the material type and at least one of the material density and the material structure of each of the respective layers.

5. The method of claim 3 wherein the layers are identified using values associated with portions of the image.

6. The method of claim 5 wherein the values are intensities of the portions of the image.

7. The method of claim 6 wherein the phase corrections are determined using a three-layer model of a skull of the subject.

8. The method of claim 7 wherein two of the three layers are assumed to have approximately identical speeds of sound, $c_i$, therein, with the other layer having a speed of sound $c_{ii}$ therein, wherein the phase corrections are determined using a phase shift determined according to:

$$\phi = 360f \sum_{n=1}^{3} D_n \left( \frac{1}{c_0} - \frac{1}{c_n} \right)$$

where $c_n$ is a speed of sound in the $n^{th}$ layer, and $D_n$ is a thickness of the $n^{th}$ layer, and wherein the speeds of sound in the layers are determined according to:

$$c_i(\rho) = (d_1 + d_3)\left[\frac{d_1 + d_2 + d_3}{c_0} - \frac{d_2}{c_{ii}} - \frac{\phi(\rho)}{360 fD}\right]^{-1}$$

where $d_1$, $d_2$, $d_3$, are thicknesses of the three layers, $\phi(\rho)$ is a measured phase shift as a function of density, and $\rho$ is density.

9. The method of claim 1 wherein the physical characteristics are associated with x-ray attenuation coefficients, $\mu$.

10. The method of claim 9 wherein the material between the sources and the desired region is bone.

11. The method of claim 9 wherein the phase corrections are related to the attenuation coefficient by a phase function including parameters derived at least partially experimentally.

12. The method of claim 11 wherein each phase correction equals $M+B\Sigma(1/\mu(x))+C\Sigma(1/\mu(x))^2$, where $\mu(x)$ is the attenuation coefficient as a function of distance x along a line of propagation between each source and the desired region, and where M, B, and C are derived at least partially experimentally.

13. The method of claim 9 wherein the amplitude corrections are related to the attenuation coefficient by an amplitude function including parameters derived at least partially experimentally.

14. The method of claim 13 wherein each amplitude correction is related to $N+F\Sigma\mu(x)+G\Sigma(\mu(x))^2$, where $\mu(x)$ is the attenuation coefficient as a function of distance x along a line of propagation between each source and the desired region, and where N, F, and G are derived at least partially experimentally.

15. The method of claim 1 wherein the layers are identified according to both material density and material structure.

16. The method of claim 1 wherein providing the image includes producing the image using magnetic resonance imaging.

17. The method of claim 1 wherein providing the image includes producing the image using computer tomography.

18. The method of claim 1 wherein the sources are piezoelectric transducer elements.

19. The method of claim 1 wherein both phase and amplitude corrections are determined.

20. A system for delivering ultrasound signals, the system comprising:
an apparatus configured to analyze an image of at least a portion of a subject intended to receive ultrasound signals between sources of the ultrasound signals and a desired region of the subject for receiving focused ultrasound signals, the apparatus configured to determine, from the image, information about different layers of the at least a portion of the subject; and
an array of sources of ultrasound signals having at least one of their relative phases and their amplitudes set in accordance with the information about each layer of the at least a portion of the subject provided by the apparatus.

21. The system of claim 20 wherein the phases are set in accordance with propagation characteristics of each layer of the at least a portion of the subject.

22. The system of claim 21 wherein the propagation characteristics are dependent upon the material type and at least one of the material density and the material structure of each layer of the at least a portion of the subject.

23. The system of claim 21 wherein the apparatus is configured to identify the layers using values associated with portions of the image.

24. The system of claim 23 wherein the values are intensities of the portions of the image.

25. The system of claim 24 wherein the apparatus is configured to determine the information about different layers of bone.

26. The system of claim 24 wherein the apparatus is configured to determine the phase corrections using a three-layer model of a skull of the subject.

27. The system of claim 23 wherein the information is associated with an x-ray attenuation coefficient, $\mu$.

28. The system of claim 27 wherein the phase corrections are related to the attenuation coefficient by a phase function including parameters derived at least partially experimentally.

29. The system of claim 27 wherein the amplitude corrections are related to the attenuation coefficient by an amplitude function including parameters derived at least partially experimentally.

30. The system of claim 20 further comprising a magnetic resonance imager coupled to the apparatus and configured to produce the image.

31. The system of claim 20 further comprising a computer tomography imager coupled to the apparatus and configured to produce the image.

32. The system of claim 20 wherein the sources are piezoelectric transducer elements.

33. A computer program product residing on a computer readable medium and comprising instructions for causing a computer to:
analyze an image of at least a portion of a subject to receive ultrasound signals between sources of the ultrasound signals and a desired region of the subject for receiving focused ultrasound signals to identify, from the image, physical characteristics of layers of material between the sources and the desired region; and
determine at least one of phase corrections and amplitude corrections for the sources depending on respective thicknesses of portions of each of the layers disposed between each source and the desired region.

34. The computer program product of claim 33 wherein the phase corrections are determined in accordance with propagation characteristics of each of the layers.

35. The computer program product of claim 34 wherein the propagation characteristics are dependent upon the material type and at least one of the material density and the material structure of each of the respective layers.

36. The computer program product of claim 33 wherein the layers are identified according to both material density and material structure.

37. The computer program product of claim 33 further comprising instructions for causing a computer to produce the image using magnetic resonance imaging.

38. The computer program product of claim 33 further comprising instructions for causing a computer to produce the image using computer tomography.

39. The computer program product of claim 33 wherein the instructions for causing a computer to identify layers of materials are for causing the computer to identify the layers of materials based upon intensities of portions of the image.

40. The computer program product of claim 33 wherein the layers are identified using values associated with portions of the image.

41. The computer program product of claim 40 wherein the values are intensities of the portions of the image.

42. The computer program product of claim 41 wherein the layers analyzed are layers of bone.

43. The computer program product of claim 41 wherein the phase corrections are determined using a three-layer model of a skull of the subject.

44. The computer program product of claim 43 wherein two of the three layers are assumed to have approximately the same speed of sound, $c_i$, therein, with the other layer having a speed of sound $c_{ii}$ therein, wherein the phase corrections are determined using a phase shift determined according to:

$$\phi = 360 f \sum_{n=1}^{3} D_n \left( \frac{1}{c_0} - \frac{1}{c_n} \right)$$

where $c_n$ is a speed of sound in the $n^{th}$ layer, and $D_n$ is a thickness of the $n^{th}$ layer, and wherein the speeds of sound in the layers are determined according to:

$$c_i(\rho) = (d_1 + d_3) \left[ \frac{d_1 + d_2 + d_3}{c_0} - \frac{d_2}{c_{ii}} - \frac{\phi(\rho)}{360 f D} \right]^{-1}$$

where $d_1$, $d_2$, $d_3$, are thicknesses of the three layers, $\phi(\rho)$ is a measured phase shift as a function of density, and $\rho$ is density.

45. The computer program product of claim 33 wherein the physical characteristics are associated with x-ray attenuation coefficients, $\mu$.

46. The computer program product of claim 45 wherein the phase corrections are related to the attenuation coefficient by a phase function including parameters derived at least partially experimentally.

47. The computer program product of claim 46 wherein each phase correction equals $M + B\Sigma(1/\mu(x)) + C\Sigma(1/\mu(x))^2$, where $\mu(x)$ is the attenuation coefficient as a function of distance x along a line of propagation between each source and the desired region, and where M, B, and C are derived at least partially experimentally.

48. The computer program product of claim 45 wherein the amplitude corrections are related to the attenuation coefficient by an amplitude function including parameters derived at least partially experimentally.

49. The computer program product of claim 48 wherein each amplitude correction is related to $N + F\Sigma\mu(x) + G\Sigma(\mu(x))^2$, where $\mu(x)$ is the attenuation coefficient as a function of distance x along a line of propagation between each source and the desired region, and where N, F, and G are derived at least partially experimentally.

50. A method of providing ultrasound signals into a subject from at least one source of an array of sources of ultrasound signals, the method comprising:

(a) transmitting ultrasound energy of a selected frequency from a selected source into the subject;

(b) receiving superimposed reflections of the transmitted energy, the reflections being from an outer surface of the subject and at least one interface inside the subject;

(c) repeating (a) and (b) using ultrasound energy of frequencies other than the selected frequency;

(d) determining a frequency difference between frequencies associated with relative extrema of the received reflections; and (e) using the determined frequency difference and a thickness, of at least a portion of material between the selected source and a desired region in the subject for receiving focused ultrasound energy signals, to determine a phase correction for the selected source.

51. The method of claim 50 further comprising:

(f) providing an image of at least a portion of a subject intended to receive ultrasound energy signals between sources of the energy signals and the desired region; and (g) identifying, from the image, the thickness of at least a portion of material between the selected source and the desired region.

52. The method of claim 50 further comprising repeating (a)–(e) for each of the sources other than the selected source.

53. The method of claim 50 wherein the phase correction is determined according to:

$$\Delta\phi = 2\pi f [(d/c_0) - (1/(2\Delta f))]$$

where $\Delta\phi$ is the phase correction, f is a frequency to be transmitted, d is the thickness, $c_0$ is the speed of sound in water, and $\Delta f$ is the frequency difference between like extrema.

54. Logic for use in a system for providing ultrasound energy into a living subject from an array of sources of ultrasound energy signals, the logic being configured to control apparatus to:

(a) transmit ultrasound energy of a selected frequency from a selected source into the subject;

(b) receive superimposed reflections of the transmitted energy, the reflections being from an outer surface of the subject and at least one interface inside the subject;

(c) repeat (a) and (b) using ultrasound energy of frequencies other than the selected frequency;

(d) determine a frequency difference between frequencies associated with relative extrema of the received reflections; and (e) use the determined frequency difference and a thickness, of at least a portion of material between the selected source and a desired region in the subject for receiving focused ultrasound energy signals, to determine a phase correction for the selected source.

55. The logic of claim 54 further configured to cause the apparatus to:

(f) provide an image of at least a portion of a subject intended to receive ultrasound energy signals between sources of the energy signals and the desired region; and (g) identify, from the image, the thickness of at least a portion of material between the selected source and the desired region.

56. The logic of claim 54 further configured to cause the apparatus to repeat (a)–(e) for each of the sources other than the selected source.

57. The logic of claim 54 wherein the logic is configured to cause the apparatus to determine the phase correction according to:

$$\Delta\phi = 2\pi f [(d/c_0) - (1/(2\Delta f))]$$

where $\Delta\phi$ is the phase correction, f is a frequency to be transmitted, d is the thickness, $c_0$ is the speed of sound in water, and $\Delta f$ is the frequency difference between like extrema.

* * * * *

UNITED STATES PATENT AND TRADEMARK OFFICE
CERTIFICATE OF CORRECTION

PATENT NO. : 6,612,988 B2
DATED : September 2, 2003
INVENTOR(S) : Maor et al.

It is certified that error appears in the above-identified patent and that said Letters Patent is hereby corrected as shown below:

<u>Column 18,</u>
Line 38, "(c)" should read -- (e) --.

Signed and Sealed this

Thirtieth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,612,988 B2
DATED : September 2, 2003
INVENTOR(S) : Maor et al.

It is certified that error appears in the above-identified patent and that said Letters Patent is hereby corrected as shown below:

<u>Title page,</u>
Item [75], Inventors, please insert as last inventor, -- Gregory T. Clement, Somerville, MA 02145 --.

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO.         : 6,612,988 B2
APPLICATION NO. : 09/738514
DATED              : September 2, 2003
INVENTOR(S)       : Kullervo Hynynen, Javier Grinfeld and Dov Maor It is certified that error appears in the above-identified patent and that said Letters Patent is hereby corrected as shown below:

Column 1, Line 8 please insert the following paragraph after the title of the invention:

--STATEMENT REGARDING FEDERALLY SPONSORED RESEARCH

This invention was made with Government support under Grant No. CA076550 awarded by the National Institute of Health. The Government has certain rights in this invention.--

Signed and Sealed this

Fourteenth Day of July, 2009

JOHN DOLL
*Acting Director of the United States Patent and Trademark Office*